United States Patent [19]

Zajic et al.

[11] 4,432,887

[45] Feb. 21, 1984

[54] DE-EMULSIFICATION AGENTS OF MICROBIOLOGICAL ORIGIN

[76] Inventors: James E. Zajic, College of Science, University of Texas, El Paso, Tex. 79968; David G. Cooper, 96 Kent St., London, Ontario, Canada, N6A 1L1

[21] Appl. No.: 298,734

[22] Filed: Sep. 2, 1981

[30] Foreign Application Priority Data

Sep. 8, 1980 [CA] Canada .................................. 359801

[51] Int. Cl.³ ........................ B01D 17/04; C02C 5/02; C02F 3/34
[52] U.S. Cl. .................................. 252/331; 210/611; 435/266
[58] Field of Search ................ 252/331; 435/101, 830, 435/170, 172, 863, 872, 822, 266; 210/611

[56] References Cited

U.S. PATENT DOCUMENTS

| | | | |
|---|---|---|---|
| 3,709,783 | 1/1973 | Tanaka et al. | 435/830 |
| 3,813,316 | 5/1974 | Chakrabarty | 435/172 |
| 3,871,956 | 3/1975 | Azarowics | 435/872 |
| 4,273,872 | 6/1981 | Zaffaroni et al. | 435/822 |
| 4,274,954 | 6/1981 | Blair | 210/611 |
| 4,350,770 | 9/1982 | Spraker | 435/172 |
| 4,355,109 | 10/1982 | Zajic et al. | 435/170 |

Primary Examiner—Richard D. Lovering
Assistant Examiner—Catherine S. Kilby
Attorney, Agent, or Firm—Murray & Whisenhunt

[57] ABSTRACT

There is provided a process for breaking or at least destabilizing oil-in-water emulsions and water-in-oil emulsions, which comprises adding to the emulsion a broth or portion of a broth resulting from the culture therein of specifically selected bacterial microorganisms of the genus Nocardia, Rhodococcus, Arthrobacter, Corynebacterium or Mycobacterium. In particular, the microorganisms, *Nocardia amarae*, *Rhodococcus aurantiacus* and *Rhodococcus rubropertinctus* have been found to yield broths, following cultivation, having exceptionally good properties as de-emulsifying agents.

14 Claims, No Drawings

DE-EMULSIFICATION AGENTS OF MICROBIOLOGICAL ORIGIN

FIELD OF THE INVENTION

This invention relates to oil-water emulsions and particularly to processes and compositions for breaking oil-in-water and water-in-oil emulsions. More specifically, it relates to processes for breaking such emulsions using compositions of microbiological origin, and the compositions themselves.

BACKGROUND OF THE INVENTION

An oil-in-water emulsion is one in which oil droplets are dispersed in a continuous aqueous phase. A water-in-oil emulsion is one in which water droplets are dispersed in a continuous oil phase. In either case, the emulsion is commonly stabilized with synthetic surfactants. Oil-in-water emulsions are best stabilized with surfactants having hydrophilic lipophilic balance (HLB value) of around 5. Water-in-oil emulsions are suitably stabilized with surfactants having HLB values of around 14.

Characteristics of emulsions vary according to the nature of the surfactant with which they are stabilized. The surfactants may be anionic, cationic or neutral. Normally the type of stabilization of the latex has an influence on the means by which they latex may be destabilized.

Breaking of such emulsions into their component phases, e.g. for separation thereof, is often of industrial importance. For example, industrial effluents often contain waste oils, the permissible levels of discharge of which are low and closely regulated. If, as often happens, the oil residues exist in the effluent as an emulsion in the aqueous phase, then separation and removal of the oil creates difficulties. First, the emulsion must be broken before effecting separation of the oil can be undertaken. Also, in industrial processes such as synthetic rubber manufacture, chemical reactions are conducted in an emulsion. The emulsion must, however, be de-stabilized and broken for efficient recovery of the product. There is therefore an industrial need for simple, rapid and efficient processes for breaking oil-water emulsions.

BRIEF DESCRIPTION OF THE PRIOR ART

A variety of ingredients are known for this purpose in the prior art. These include alkaline salts including alkaline salts of organic acids, for example sodium di-2-ethylhexylsulphosuccinate, commercially available as Aerosol OT, reported to be effective in de-emulsifying seawater/navy fuel oil emulsions. This and other prior art reagents are described by R. C. Little, "Breaking Emulsions of Water in Navy Fuel Oils", Fuel, 53 244–252(1974).

Reagents added to break oil-water emulsions should not only be effective in such applications. They should also be highly efficient so that only small quantities need to be used. In addition, they should not themselves create environmental problems, so that their residual presence in industrial effluents, resulting from effective additions thereof, is not harmful.

SUMMARY OF THE INVENTION

It is an object of the present invention to provide a novel process for breaking oil-water emulsions.

It is a further object to provide novel compositions of matter useful in breaking oil-water emulsions, of both the oil-in-water type and the water-in-oil type.

The present invention provides emulsion breaking compositions of microbiological origin, which have very high efficiency in breaking both types of emulsion. They are the products of culturing bacterial species of the genus Norcardia, Rhodococcus, Arthrobacter, Corynebacterium or Mycobacterium in a growth promoting medium. Not only do the products exhibit high emulsion breaking efficiency, so that they can be used in relatively small amounts, but also they are of biological origin and are biologically harmless, so that their use does not present any environmental hazard. The compositions most useful in the present invention are the culture broths, or portions thereof, resulting from the fermentation of one or more bacteria selected from the species *Nocardia amarae, Rhodococcus aurantiacus, Rhodococcus rubropertinctus, Arthrobacter paraffineus, Corynebacterium fascians, Corynebacterium hydrocarbooxydous, Mycobacterium cuneatum* and *Mycobacterium petroleophillum.*

In accordance with the present invention there is provided a process of destabilizing an oil-in-water or water-in-oil emulsion, which comprises treating the emulsion with an effective amount of at least a portion of a liquid broth resulting from the culturing and growth therein of a bacterial micro-organism on a carbon-containing substrate under growth promoting conditions, said bacterial microorganism being one which produces effective de-emulsifying fermentation products and selected from the genus Nocardia, the genus Rhodococcus, the genus Arthrobacter, the genus Corynebacterium and the genus Mycobacterium.

DESCRIPTION OF THE PREFERRED EMBODIMENTS

The fermentation products useful in the present invention do not appear to show any particular pattern or common characteristics between them, in respect of the microorganisms from which they are derived, the substrates from which they are grown, etc. It does, however, appear from results obtained that substantially all strains of a given microbiological bacterial species as set out above will yield fermentation products useful in the present invention, with the possible exception of the *Arthrobacter paraffinius* species where anomalous results among strains have been located. The precise ones of the bacterial species which will yield useful products in the present invention, however, appears to be quite unpredictable. For example, among the *Nocardia species,* there has been found one species, *Nocardia amarea,* which produces highly effective products in the present invention, whereas other species of *Nocardia genus* are to all intents and purposes useless. In the same way, some species from the genus Corynebacterium have been found useful, and others of no particular utility. Extensive testing and screening of products from the Pseudomonas genus have not shown any useful products for the present invention. Some species show their greatest utility in breaking neutrally stabilized emulsion, others in breaking anionically stabilized emulsions, and others in breaking cationically stabilized emulsions. One of the particularly important and surprising features of the invention is that certain species will break all these types of emulsions. No particular similarities between useful species, or between highly useful species, or between useless species for purposes of the present invention have been established. It is therefore unexpected and quite surprising that some outstandingly effective products should be located in accordance with the present invention.

The most preferred bacterial species for use in the present invention are Nocardia amarea, Rhodococcus aurantiacus, and Rhodococcus rubropertinctus. All three of these species have been found to produce culture broths of outstanding efficiency in breaking not only water-in-oil emulsions but also oil-in-water emulsions, at relatively low concentrations. Whilst the other species referred to above yield fermentation broths which have a considerable degree of utility in the present invention, the culture broths from the three aforementioned species have outstanding utility, and show considerable commercial potential.

Both R. aurantiacus and R. rubropertinctus produce broths having the most unusual and unexpected combination of properties, of high ability to break both neutral and cationic stabilized emulsions, along with some ability to break anionic emulsions also. Other species having such unusual combinations of properties are shown in the examples below.

It may be that only a portion of the resultant culture broth is actually effective in de-emulsification. The precise component responsible for the action has not been identified with certainty. However, the other components of the culture broth are not harmful to the de-emulsification aspect, and so it is preferred according to the present invention to use portions of the entire fermentation broth as de-emulsification agents. The cellular products in general appear to be the most efficient components. The presence of living residual culture cells in the material as added for de-emulsification purposes is not essential. Experimental results indicate that it is immaterial whether viable cultures remain. For example, as shown in the following illustrative examples, the culture broth can be heat treated to an extent which kills all residual viable organisms, before it is used in de-emulsification processes. It appears to be equally effective in this form, as in the form containing live cultures. Some at least of the whole cells are more effective in the present invention than extracellular product. The particular nature of the cells themselves appears to have a significant impact upon their ability to break the micelles of an emulsion.

The various species of bacteria are grown, in the culture broth, in the presence of a carbon providing substrate, such as hexadecane, or a soluble carbon providing substrate such as yeast extract or glucose. However, the precise substrate which is chosen for growth purposes again does not appear to be important. Culturing of the microbiological species takes place according to known procedures and under standard conditions, as known to those skilled in the art.

Preferred amounts of whole culture broth for use in the present invention are from about 0.1 to about 2 volumes of broth per 10 volumes of emulsion. Most preferred is from about 0.2 to about 1 volume of broth per 10 volumes of emulsion.

The invention will be further described with reference to the following specific examples:

EXAMPLE 1

Standard Emulsion Preparations and Measurements

Standard water-in-oil (W/O) emulsions were prepared for test purposes using kerosene and water, together with a synthetic surfactant. For each test batch of emulsion, 4 ml of a 0.068% aqueous solution of L92 Pluronic surfactant (BASF, Wyandotte Corporation) was added to a test tube with 6 ml of kerosene, and vortexed for about 2 minutes until the maximum emulsion was obtained. In use for testing the emulsion-breaking properties of the samples, the sample was added to the emulsion and the system was further vortexed to cause mixing.

Standard oil-in-water (O/W) emulsions were also prepared, in analogous fashion, using a mixture of two surfactants, namely 0.072% Tween 60 and 0.028% Span 60 surfactants in the aqueous phase. L92 Pluronic, Tween 20 and Span 60 are neutral surfactants.

A water-in-oil (W/O) emulsion was prepared from a kerosene solution of span 80, an oleophilic surfactant, produced by dissolving 0.078 g of surfactant in 100 ml kerosene, combining the 5 ml of the kerosene solution and 5 ml water in a test tube and vortexing.

An oil-in-water (O/W) emulsion stabilized with an anionic surfactant was prepared. For this, an aqueous solution of Avirol A-200 anionic surfactant was prepared by dissolving 0.01 g of the surfactant in 100 ml water. A dilute solution of NaOH was used to increase the pH to the 8.5–9.5 range. To make the test emulsion, 5 ml of the aqueous solution and 5 ml of kerosene were vortexed in a test tube.

An oil-in-water (O/W) emulsion stabilized with a cationic surfactant was also prepared. An aqueous solution of Rohm and Haas surfactant RW-150 was made by dissolving 0.63 g surfactant in 100 ml water. The pH was adjusted to the range 5.0–6.0 with HCl. A test tube containing 5 ml of this solution and 5 ml kerosene was vortexed until a maximum emulsion was obtained.

To measure the emulsion-breaking properties of a test sample, an assumption is made that the emulsion breakdown can be approximated as a first order reaction, so that a plot can be made of the logarithm of the percent of the volume which was an emulsion against the time of measurement. Then the slope of the plot can be used to calculate the half-life of the emulsion:

$$t^{\frac{1}{2}} = \frac{-0.301}{\text{slope}}$$

Control experiments were done using appropriate samples of sterile media.

EXAMPLE 2

Bacterial samples were grown under standard, growth-promoting conditions in a liquid culturing broth, and the resultant whole broths were tested as emulsion breakers as described in Example 1.

The growth medium was an aqueous mineral salts medium of the following composition, containing 4% hexadecane as substrate:

| | |
|---|---|
| NaNO$_3$ | 2.0 g/l |
| NH$_4$NO$_3$ | 4.0 g/l |
| K$_2$HPO$_4$ | 4.0 g/l |
| KH$_2$PO$_4$ | 6.0 g/l |
| MgSO$_4$.7H$_2$O | 0.2 g/l |
| CaCl$_2$ | 0.001 g/l |
| FeSO$_4$ | 0.001 g/l |
| EDTA | 0.0014 g/l |

The bacteria chosen and cultured were various species of the genus Corynebacterium. Then, after culturing for seven days in some cases, eleven days in others, 0.5 ml aliquots of the whole broth were added to the test emulsions, as previously described, and the half-lives of the emulsion determined. The results are given in the following Table I:

TABLE I

| Bacteria | Biomass after 11 days g/l | Half-life, in hours: | | | | |
|---|---|---|---|---|---|---|
| | | L92 O/W | T/S O/W | Span 80 W/O | A-200 O/W | RW-150 O/W |
| C. hydrocarbooxydans (ATCC 21767) | 1.0 | 27 | 14 | 23 | 13 | 200 |
| C. hydrocarboclastus (NRRL B-5631) | 2.5 | 100 | 20 | 15 | 9 | 83 |
| C. dioxydans (ATCC 21766) | 3.7 | 95 | 37 | 10 | 4 | 20 |
| C. petrophilum (ATCC 21404) | 6.2 | 8 | 55 | 1 | 1 | 3 |
| C. lepus[1] | 2.6 | 1 | 6 | 14 | 1 | 1 |
| C. fascians (ICPB CF15) | 7.8 | 7 | 20 | 32 | 3 | 5 |
| Control | | 200 | 200 | 200 | 200 | 200 |

[1]Culture deposited in ICPB (California).

Of the above bacteria, the broth products from cultivating all of the various Corynebacterium species tested show a degree of utility for breaking emulsions. The most successful and promising all round are *C. fascians* (further reported in Example 3 below) and *C. lepus*. The differences between them are unpredictable and not fully understood.

EXAMPLE 3

A large number of individual strains of bacteria species Corynebacterium fascians were grown in culture medium as previously described, and the culture broths produced were tested for their emulsion breaking capabilities as in Example 2. The culture medium, substrate and time of growth were also as previously described. The results are given in Table II.

TABLE II

| Bacteria Strains | Half-life O/W, L92 Stabilized (hours) | Half-life O/W, T/S Stabilized (hours) |
|---|---|---|
| C. fascians NRRL B-190 | 6.3 | 200 |
| C. fascians ICPB CF15 | 8.9 | 200 |
| C. fascians ICPB CF16 | 77 | 200 |
| C. fascians ICPB CF17 | 24 | 200 |
| C. fascians ICPB CF21 | 17 | 59 |
| C. fascians ATCC 12474 | 2.7 | 200 |
| Control | 200 | 200 |

All of these strains show a degree of utility in connection with breaking W/O emulsions. However, strain ICPB CF21 in addition shows utility in breaking O/W emulsions also.

EXAMPLE 4

Using cultivation techniques, test procedures and results calculated as described in the previous examples, bacterial strains from the genus Nocardia, Rhodococcus, Mycobacterium and Arthrobacter were cultured and the resulting broths evaluated as emulsion breaking compositions. The microorganisms grown, and the results obtained, are given in Table III. With the exception of the Nocardia and Arthrobacter species the culture medium and substrates were as detailed in Example II. Whilst the Arthrobacter and Nocardia species were cultured on the same substrate, hexadecane, the culture medium was varied slightly to include 0.01 g/l K Cl and 2.0 g/l sodium nitrate, to reduce the amount of dipotassium hydrogen phosphate to 1.0 g/l the amount of potassium di-hydrogen phosphate to 0.5 g/l to increase the amount of calcium chloride to 0.011 g/l and the amount of ferrous sulphate to 0.01 g/l and to eliminate the ammonium nitrate and the EDTA. Also, the culture medium for the species Mycobacterium cuneatum included 0.1% yeast extract, and kerosene as substrate.

TABLE III

| Bacterium | Half-life O/W, L92 Stabilized (hours) | Half-life O/W, T/S Stabilized (hours) | Half-life W/O, Span 80 (hours) | Half-life A-200 O/W (hours) | Half-life RW-150 O/W (hours) |
|---|---|---|---|---|---|
| Nocardia amerae NRRL B-8176 | 0.1 | 3.3 | 13 | 16 | >200 |
| Rhodococcus aurantiacus 80001 | 0.1 | 0.8 | <1 | 160 | 14 |
| Rhodococcus rubropertinctus 60003 | 0.1 | 0.3 | 22 | 42 | 19 |
| Arthrobacter paraffineus | 4.6 | 9.0 | 2 | >200 | 36 |
| Mycobacterium cuneatum ATCC 21498 | 49 | 62 | 28 | 39 | <1 |
| Mycobacterium petroleophillum ATCC 21497 | 120 | 67 | >200 | >200 | <1 |
| Nocardia erythropolis ATCC 4277 | >200 | >200 | 18 | 21 | 15 |
| Mycobacterium parafortuitum ATCC 19686 | >200 | >200 | 20 | <1 | 14 |
| Mycobacterium rhodochrous ATCC 19067 | 150 | >200 | 16 | <1 | 74 |
| Mycobacterium rhodochrous ATCC 13808 | 150 | >200 | | | |
| Mycobacterium brevicale ATCC 15313 | >200 | >200 | 24 | >200 | <1 |
| Control | >200 | >200 | >200 | >200 | >200 |

The broths from species Nocardia amarae and the Rhodococcus species show good results in breaking both W/O and O/W emulsions. The other Nocardia species tested shows various effects in the different emulsions. Essential replications of the results with Rhodococcus species were obtained when the same species and strains thereof were grown on a soluble glucose substrate as carbon source instead of the insoluble hexadecane carbon source.

It is also noteworthy that, at least within the Mycobacterium species, and presumably in other species, different strains with the same species give essentially the same results. *Arthrobacter paraffineus* appears to be an exception in this respect. The above results related to a "Strain 2". Neither strain 1 nor strain 3 gave worthwhile results.

When similar experiments were conducted with various species of Pseudomonas, namely species *aeruginosa* (two strains), *fluorescens* (two strains), *rubescens*, *alkanolytica* and *oleovorans*, no worthwhile results were obtained when their cultivation broths were added to oil-water emulsions.

EXAMPLE 5

The three species of bacteria whose broth was demonstrated above to have outstanding de-emulsification properties, namely *Nocardia amarae, Rhodococcus* aurantiacus and *R. rubropertinctus*, were grown in shake flasks on a variety of media. These included soluble carbon sources such as glucose and yeast extract, an insoluble carbon source (hexadecane) and mixtures of both. The resulting broths were tested as previously described for de-emulsification properties. Apart from the substrate, the growth media were as previously described.

The results indicated that N amarae caused good de-emulsification of both W/O and O/W test systems, on all substrates. There is however a deterioration in its abilities in older culture systems when using mixed substrates—the broth after five days culturing on yeast extract and hexane mixture is a more powerful de-emulsifier than the same broth after ten days culturing.

With respect to culture *R aurantiacus*, the best growth substrate was hexadecane, alone or in admixture. The species produced a highly effective de-emulsification broth on all tested substrates, however. The substrate used with *R. rubropertinctus* had little effect on the de-emulsification properties of the broth, but again the broth after five days culturing was more effective than after eleven days culturing.

EXAMPLE 6

An experiment was done to determine the heat stability of the products from the three outstanding de-emulsifying bacteria. The organisms were grown for five days on 1% yeast extract and 4% glucose or 1% yeast extract and 4% hexadecane. Sterile samples were removed from each flask. The flasks were then autoclaved (120° C.) for 10 minutes and then cooled to room temperature. A comparison was then made between the activity of the heat killed and unheated samples on the test emulsions. The results are shown in Table IV. In general there is very little change in the de-emulsification ability of all three bacteria after autoclaving (121° C. for 30 minutes). Several pairs of data do show some loss in activity, but the half-lives are not increased by more than 20 hours. In some cases there is even a slight improvement in de-emulsification ability.

TABLE IV

| | $t_{\frac{1}{2}}$ of O/W, L92 | | $t_{\frac{1}{2}}$ of O/W, T/S | |
|---|---|---|---|---|
| | Unheated | Heated | Unheated | Heated |
| 1. 1% yeast extract, 4% glucose | | | | |
| N. amarae | 6.8 | 22 | 8.4 | 18 |
| R. aurantiacus | 29 | 56 | 14 | 26 |
| R. rubropertinctus | 34 | 9.3 | 34 | 54 |
| 2. 1% yeast extract, 4% hexadecane | | | | |
| N. amarae | 54 | 37 | 28 | 27 |
| R. aurantiacus | 36 | 34 | 26 | 37 |
| R. rubropertinctus | 124 | 154 | 120 | 150 |

We claim:

1. A process of destabilizing an oil-in-water or water-in-oil emulsion, which comprises treating the emulsion with an effective amount of at least a portion of the liquid broth resulting from the culturing and growth therein of a bacterial microorganism on a carbon-containing substrate under growth promoting conditions, said bacterial microorganism being one which produces effective de-emulsifying fermentation products for the type of emulsion chosen and being selected from the group of species consisting of Nocardia amarae, *Nocardia erythropolis, Rhodococcus aurantiacus, Rhodococcus rubropertinctus, Arthrobacter paraffineus, Corynebacterium hydrocarboclastus, Corynebacterium oxydans, Corynebacterium petrophilum, Corynebacterium lepus, Corynebacterium fascians, Corynebacterium hydrocarbooxydans, Mycobacterium cuneatum, Mycobacterium petroleophillum, Mycobacterium parafortuitum, Mycobacterium rhodochrous* and *Mycobacterium brevicale*.

2. The process of claim 1 wherein an oil-in-water emulsion stabilized with a neutral surfactant is destabilized by treating the emulsion with liquid broth from the culturing-growth therein of a bacterial microorganism selected from the group of species consisting of *Corynebacterium hydrocarbooxydans, Corynebacterium hydrocarboclastus, Corynebacterium oxydans, Corynebacterium petrophilum, Corynebacterium lepus, Corynebacterium facsians, Nocardia amarae, Rhodococcus aurantiacus, Rhodococcus rubropertinctus, Arthrobactaer parafineus* and *Mycobacterium cuneatum*.

3. The process of claim 2 wherein the bacterial microorganism is selected from the group of species consisting of *Corynebacterium lepus, Nocardia amarae, Rhodococcus aurantiacus,* and *Rhodococcus rubropertinctus*.

4. The process of claim 1 wherein an oil-in-water emulsion stabilized with an anionic surfactant is destabilized by treating the emulsion with liquid broth from the culturing and growth therein of a bacterial microorganism selected from the group of species consisting of *Corynebacterium hydrocarboxydans, Corynebacterium hydrocarboclastus, Corynebacterium oxydans, Corynebacterium petrophilum, Corynebacterium lepus, Corynebacterium fascians, Nocardia amarae, Nocardia erythropolis, Mycobacterium parafortuitum* and *Mycobacterium rhodochrous*.

5. The process of claim 4 wherein the bacterial microorganism is selected from the group of species consisting of *Corynebacterium oxydans, Corynebacterium petrophilum, Corynebacterium lepus, Corynebacterium fascians, Mycobacterium parafortuitum* and *Mycobacterium rhodochrous*.

6. The process of claim 1 wherein an oil-in-water emulsion stabilized with a cationic surfactant is destabilized by treating the emulsion with liquid broth from the culturing and growth therein of a bacterial microorganism selected from the group of species consisting of *Corynebacterium hydrocarboclastus, Corynebacterium oxydans, Corynebacterium petrophilum, Corynebacterium lepus, Corynebacterium fascians, Rhodococcus aurantiacus, Rhodococcus rubropertinctus, Arthrobacter parafineus, Mycobacterium cuneatum, Mycobacterium petroleophillum, Nocardia erythropolis, Mycobacterium parafortuitum, Mycobacterium rhodochrous* and *Mycobacterium brevicale*.

7. The process of claim 6 wherein the bacterial microorganism is selected from the group of species consisting of *Corynebacterium petrophilum, Corynebacterium lepus, Corynebacterium fascians, Mycobacterium cuneatum, Mycobacterium petroleophillum,* and *Mycobacterium brevicale*.

8. The process of claim 1 wherein a water-in-oil emulsion is destabilized by treating the emulsion with liquid broth from the culturing and growth therein of a bacterial microorganism selected from the group of species consisting of *Corynebacterium hydrocarbooxydans, Corynebacterium hycrocarboclastus, Corynebacterium oxydans, Corynebacterium petrophilum, Corynebacterium lepus, Corynebacterium fascians, Nocardia amarae, Rhodococcus aurantiacus, Rhodococcus rubropertinctus, Arthrobacter parrafineus, Nocardia erythropolis, Mycobacterium parafortuitum, Mycobacterium rhodochrous* and *Mycobacterium brevicale*.

9. The process of claim 7 wherein the microorganism is selected from the group of species consisting of *Corynebacterium petrophilum, Nocardia amarae, Rhodococcus aurantiacus, Rhodococcus rubropertinctus* and *Arthrobacter paraffineus*.

10. The process of claim 9 wherein the water-in-oil emulsion is stabilized with a neutral surfactant.

11. The process of claim 1 wherein the treating composition comprises whole culture broths.

12. The process of claim 11 in which from about 0.2 to about 1 volume of whole broth is added per 10 volumes of emulsion.

13. The process of claim 12 wherein the liquid broth is prepared by growing the bacterial microorganism on a hydrocarbon substrate.

14. The process of claim 12 wherein the liquid broth is prepared by growing the bacterial microorganism on a soluble carbohydrate substrate.

* * * * *